(12) United States Patent
Bergman et al.

(10) Patent No.: US 10,085,939 B2
(45) Date of Patent: Oct. 2, 2018

(54) COMPOSITION OF DEXIBUPROFEN TRANSDERMAL HYDROGEL

(71) Applicant: Strides Shasun Limited, Tamil Nadu (IN)

(72) Inventors: Jeffrey Stuart Bergman, Hertfordshire (GB); Sampathkumar Devarajan, Chennai (IN); Selvakumar Ramalingam, Tamil Nadu (IN); Anandsenthil Vel Palanisamy, Tamil Nadu (IN)

(73) Assignee: Strides Shasun Limited (IN)

( * ) Notice: Subject to any disclaimer, the term of this patent is extended or adjusted under 35 U.S.C. 154(b) by 0 days.

(21) Appl. No.: 14/824,787

(22) Filed: Aug. 12, 2015

(65) Prior Publication Data
US 2015/0342879 A1 Dec. 3, 2015

Related U.S. Application Data

(63) Continuation of application No. 13/525,432, filed on Jun. 18, 2012, now abandoned.

(51) Int. Cl.
| | | |
|---|---|---|
| *A61K 9/06* | (2006.01) | |
| *A61K 31/192* | (2006.01) | |
| *A61K 9/00* | (2006.01) | |
| *A61K 47/02* | (2006.01) | |
| *A61K 47/12* | (2006.01) | |
| *A61K 47/38* | (2006.01) | |
| *A61K 47/10* | (2017.01) | |
| *A61K 47/18* | (2017.01) | |
| *A61K 47/32* | (2006.01) | |

(52) U.S. Cl.
CPC .............. *A61K 9/06* (2013.01); *A61K 9/0014* (2013.01); *A61K 31/192* (2013.01); *A61K 47/02* (2013.01); *A61K 47/12* (2013.01); *A61K 47/18* (2013.01); *A61K 47/10* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 4,684,666 | A * | 8/1987 | Haas | A61K 31/19 514/557 |
| 6,399,093 | B1 * | 6/2002 | Petrus | A61K 9/0014 424/448 |
| 7,459,171 | B2 * | 12/2008 | Cevc | A61K 9/1272 210/321.75 |
| 2001/0014711 | A1 * | 8/2001 | Levy | C10M 111/04 524/406 |
| 2001/0023261 | A1 * | 9/2001 | Ryoo | A61K 9/0014 514/772 |
| 2002/0015712 | A1 * | 2/2002 | Mcbride | A61K 9/0024 424/400 |
| 2002/0102301 | A1 * | 8/2002 | Schwarz | A61K 9/1075 424/468 |
| 2003/0170295 | A1 * | 9/2003 | Kim | A61K 9/7061 424/449 |
| 2005/0025778 | A1 * | 2/2005 | Cormier | A61B 17/205 424/185.1 |
| 2005/0136084 | A1 * | 6/2005 | Fukasawa | A61K 8/0208 424/401 |
| 2005/0239894 | A1 * | 10/2005 | Steiger | A61K 9/0014 514/567 |
| 2006/0257488 | A1 * | 11/2006 | Hubbard | A61K 9/0024 424/486 |
| 2007/0020325 | A1 * | 1/2007 | Kuribayashi | A61K 9/0014 424/448 |
| 2010/0137443 | A1 * | 6/2010 | Carter | A61K 9/0014 514/570 |

OTHER PUBLICATIONS

Adams, J. Pharm Pharmac., 1976, vol. 28, pp. 256-257.*

* cited by examiner

*Primary Examiner* — Katherine Peebles

(57) ABSTRACT

Stable non-alcoholic transdermal hydrogel of dexibuprofen was prepared by using a simple manufacturing process, and the experimental trials showed that the pH modifying agent, antioxidant and water miscible solvent are the essential excipients to obtain stable non-alcoholic transdermal hydrogel of dexibuprofen. The dexibuprofen hydrogel prepared using carbopol as a gelling polymer produced an opaque gel, whereas hydrogel prepared using hyroxypropyl methylcellulose (HPMC) as a gelling polymer produced a transparent gel. There was no significant changes observed with respect to physical description, pH, assay and particularly to the related substance values when the hydrogels were subjected to the stability study at accelerated condition (40° C./75% RH) for 3 months in laminated tubes.

4 Claims, No Drawings

COMPOSITION OF DEXIBUPROFEN TRANSDERMAL HYDROGEL

CROSS-REFERENCE TO RELATED APPLICATION

This continuation application claims the benefit of U.S. patent application Ser. No. 13/525,432, filed Jun. 18, 2012, which is incorporated herein by reference.

TECHNICAL FIELD OF THE INVENTION

The present invention relates to a topical pharmaceutical composition containing dexibuprofen [(S)-2-(4-isobutylphenyl) propionic acid] and the process for preparing the same.

BACKGROUND OF THE INVENTION

Ibuprofen (2-(4-isobutylphenyl) propionic acid) has one chiral center, thus there are two enantiomers, S (+)-ibuprofen (dexibuprofen) and R (−)-ibuprofen, also known as (S+)-ibuprofen and (R−)-ibuprofen. The racemic form consisting of equal amounts of S(+)-ibuprofen and R(−)-ibuprofen is exclusively used in the currently available commercial preparations, as well as the water soluble salts of ibuprofen such as lysinate, arginate, sodium, potassium etc are also used. Racemic ibuprofen has relatively high melting point (about 78° C.), while both stereoisomer's of ibuprofen, S (+)-ibuprofen and R (−)-ibuprofen, melt at 52° C. to 54° C. All the different forms of ibuprofen are poorly soluble in water Notably, the S (+) form alone appears to be responsible for the anti-inflammatory activity, not the R (−) form (S. Adams et al., Curr. Med. Res. Opin., 3, 552 (1975); S. Adams et al., J. Pharm. Pharmaco., 28, 256-257 (1976)).

U.S. Pat. No. 5,093,133 discloses hydroalcoholic gel formulations of (S)-ibuprofen as an effective vehicle for percutaneous delivery of (S+)-ibuprofen through the skin. In this patent, the hydroalcoholic gel of (S+)-ibuprofen is prepared by using 40 to 60% of alcohol; 0-20% of a non-volatile solvent; 2.0 to 5.0% of gelling agents; sufficient base, to adjust the pH to between 3.5 to 6.0; and water.

U.S. Pat. No. 5,767,161 discloses a pharmaceutical composition in the form of cream, foam or stick containing 2.5-10% by weight (S)-2-(4-isobutylphenyl)propionic acid, 20-30% by weight ethanol and 5-50% by weight propylene glycol, the ratio of ethanol to propylene glycol is 0.6-1 to 4:1. This patent also reports an increase in cutaneous permeation of the active ingredient with respect to those obtained by known topical pharmaceutical compositions containing an equivalent or higher amount of Ibuprofen.

U.S. Pat. No. 6,368,618 discloses a novel two phase liquid topical formulation for delivery of S(+)-ibuprofen, which is characterized by enhanced transdermal absorption and efficacy. In this patent two phase system consist of an aqueous and oil phases, the oil phase contains a relatively high concentration of the S (+)-ibuprofen making it directly available for partitioning into the stratum corneum without the rate-limiting diffusion process from the inert oil phase as in a conventional cream.

U.S. Pat. No. 5,696,165 discloses phaimaceutical compositions for oral, rectal or topical administration containing (S)-Ibuprofen sodium salt as an active ingredient. This patent reports that the S(−)sodium 2-(4-isobutylphenyl) propionate has advantage over S(+) 2-(4-isobutylphenyl)propionate for preparing pharmaceutical compositions containing water and additional formulation advantage is that S(−) sodium 2-(4-isobutylphenyl)propionate will resist esterification with excipients which contain a hydroxyl group for example mono-, di-, tri- or polyhydric alcohols.

As disclosed in the prior arts dexibuprofen is formulated into topical formulations either using high amount of alcohol or using a two phase system to enhance the transdermal absorption and efficacy.

Thus, there is a constant need to formulate topical formulation of dexibuprofen which can be prepared by simple manufacturing process and should also provide an effective transdermal penetration.

OBJECTIVES OF THE INVENTION

One of the objective(s) of the present invention is to prepare a non-alcoholic transdermal hydrogel of dexibuprofen.

Another objective of the present invention is to prepare a clear transparent non-alcoholic transdermal hydrogel of dexibuprofen.

SUMMARY OF THE INVENTION

The present invention relates to a pharmaceutical composition for topical use containing dexibuprofen, more particularly to a non-alcoholic dexibuprofen transdermal hydrogel and process of preparing the same. Stable non-alcoholic transdermal hydrogel of dexibuprofen was prepared by using a simple manufacturing process, and the experimental trials showed that the pH modifying agent, antioxidant and water miscible solvent are the essential excipients to obtain stable non-alcoholic transdermal hydrogel of dexibuprofen. The dexibuprofen hydrogel prepared using carbopol as a gelling polymer produced an opaque gel, whereas hydrogel prepared using hyroxypropyl methylcellulose (HPMC) as a gelling polymer produced a transparent gel. There was no significant changes observed with respect to physical description, pH, assay and particularly to the related substance values when the hydrogels were subjected to the stability study at accelerated condition (40° C./75% RH) for 3 months in laminated tubes.

DETAILED DESCRIPTION OF THE INVENTION

The present invention relates to a pharmaceutical composition for topical use containing dexibuprofen, more particularly to a non-alcoholic transdermal hydrogel of dexibuprofen and process of preparing the same.

Topical NSAIDs preparations are commonly use to treat pain and inflammation associated with joints and muscles. Topical NSAIDs have three major advantages over oral treatment of pain and inflammation associated with joints and muscles:

i) higher concentrations of NSAIDs are delivered to the desire site;
ii) only 1-3% of NSAIDs is systemically absorbed, reducing the possibility of gastrointestinal upset or ulcers; and
iii) low blood levels reduce the incidence of drug interactions.

Ibuprofen topical preparations are available for the treatment of pain and inflammation associated with joints and muscles. Ibuprofen (2-(4-isobutylphenyl) propionic acid) has one chiral center, thus there are two enantiomers, S (+)-ibuprofen (dexibuprofen) and R (−)-ibuprofen, also known as (S)-ibuprofen and (R)-ibuprofen. Notably, the S(+) form alone appears to be responsible for the anti-inflammatory activity, not the R(−) form (S. Adams et al., Curr. Med. Res. Opin. 3, 552 (1975); S. Adams et al., J. Pharm. Pharmaco., 28, 256-257 (1976)).

The popular topical NSAIDs preparations include cream, ointment and gel, now a day's topical hydrogels are gaining popularity because of their cooling effect, and non-greasy nature.

In the prior arts, dexibuprofen is formulated into topical gel formulations either using high amount of alcohol or using a two phase system to enhance the transdermal absorption and efficacy.

The present invention relates to a pharmaceutical composition for topical use containing dexibuprofen more particularly to non-alcoholic transdermal hydrogel of dexibuprofen and process of preparing the same.

According to the present invention, process of preparing a non-alcoholic transdermal hydrogel of dexibuprofen comprising the steps of:
- step (i) disperse the gelling polymer(s) in purified water and allow it to soak overnight,
- step (ii) dissolve the preservative(s) in purified water and then disperse dexibuprofen in it,
- step (iii) dissolve the menthol in triethanolamine,
- step (iv) mix step (iii) with step (ii) with continuous stirring,
- step (v) mix propylene glycol and PEG 400; add this mixture to transcutol-P followed by the addition of lavender oil and mix well,
- step (vi) add step (v) to step (iv) and mix well, and
- step (vii) finally add step (vi) to step (i) with constant stirring to obtain homogenous gel.

According to the present invention non-alcoholic transdermal hydrogel of dexibuprofen may be transparent or translucent or opaque in nature.

Other than active ingredient dexibuprofen, the present invention comprises one or more pharmaceutically acceptable excipient(s) selected from the group comprising of gelling agent, pH modifying agent, spreadability modifying agent, water miscible solvent, soothing agent, preservative, antioxidant, surfactant, chelating agent, permeation enhancer, antifoaming agent and flavoring agent etc.

According to the present invention one or more gelling agent(s) can be selected from the group comprising of carbomer, hydroxypropyl methylcellulose (HPMC), hydroxyethyl cellulose (HEC), poloxamer, hydroxypropyl cellulose (HPC), methylcellulose (MC), collagen, gelatin, agar, alginic acid and its sodium salts such as sodium alginate, carrageenans and its sodium or potassium salts, tragacanth, pectin, guar gum, xanthan gum, gellan gum, polyacrylamide, polyvinyl alcohol, polyethylene and its co-polymers and the like.

According to the present invention one or more pH modifying agent(s) can be selected from the group comprising of sodium hydroxide, citric acid, sodium citrate, triethanolamine, diethanolamine and the like.

According to the present invention one or more soothing agent(s) can be selected from the group comprising of menthol, thymol, camphor and the like.

According to the present invention one or more preservative(s) can be selected from the group comprising of sodium salts of methyl paraben, propyl paraben, other preservatives like salicylic acid and its salts, chlorhexidine hydrochloride, phenoxyethanol, sodium benzoate, methyl para-hydroxybenzoate, ethyl para-hydroxybenzoate, propyl para-hydroxybenzoate, butyl para-hydroxybenzoate and the like.

According to the present invention at least one oil-soluble and/or water soluble antioxidant(s) can be selected from the group comprising of butylated hydroxytoluene (BHT), ascorbyl palmitate, butylated hydroxanisole (BHA), phenyl-α-naphthylamine, hydroquinone, propyl gallate, nordihydroguiaretic acid, ascorbic acid, sodium benzoate, sodium metabisulfite, sodium bisulfite, sodium thiosulfite, sodium folinaldehyde sulfoxylate, isoascorbic acid, thioglyerol, thiosorbitol, thiourea, thioglycolic acid, cysteine hydrochloride, 1,4-diazobicyclo-(2,2,2)-octane and the like, According to the present invention one or more surfactant(s) can be selected from the group comprising of sodium alkyl sulfates such as sodium lauryl sulfate and sodium myristyl sulfate, sodium N-acyl sarcosinates such as sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate, N-acyl glutamates such as N-palmitoyl glutamate, N-methylacyltaurin sodium salt, N-methylacyl-alanine sodium salt, sodium a-olefin sulfonate, sodium dioctylsulfosuccinate; N-alkylaminoglycerols such as N-lauryl-diaminoethylglycerol and N-myristyldiaminoethylglycerol, N-alkyl-N-carboxymethylammonium betaine, sodium 2-alkyl-1-hydroxyethylimidazo line betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, pluronic type surface active agent, and polyoxyethylenesorbitan aliphatic acid esters such as polyoxyethylenesorbitan monooleate and polyoxyethylenesorbitan monolaurate and the like.

According to the present invention one or more spreadability modifying agent(s) can be selected from the group comprising of polyethylene glycol, propylene glycol, glycerin, light liquid paraffin and the like.

According to the present invention one or more water miscible solvent (s) can be selected from the group comprising of polyethylene glycol, propylene glycol, glycerin and the like. The water miscible solvent (i.e. a cosolvent) will be present, to assist in dissolving the active agent other essential excipients.

According to the present invention one or more permeation enhancer(s) can be selected from the group comprising of caprylic acid and its derivatives, polyoxylglycerides and its derivatives, triglycerides and its derivatives, lauric acid and its derivatives, oleic acid and its derivatives, diethylene glycol monoethyl ether (Transcutol-P), and the like.

According to the present invention one or more chelating agent(s) can be selected from the group comprising of ethyl enediaminetetraaceti c acid (EDTA), sodium EDTA, disodium EDTA, citric acid, tartaric acid and the like.

According to the present invention one or more antifoaming agents can be selected from the group comprising of simethicone, dimethicone and the like.

According to the present invention one or more flavoring agent(s) can be selected from the group comprising of lavender oil, rose oil, menthol, anethole, carvone, eugenol, limonene, ocimene, n-decylalcohol, citronellol, α-terpineol, methyl salicylate, methyl acetate, citronellyl acetate, cineole, linalool, ethyl linalool, vanillin, thymol, spearmint oil, peppermint oil, lemon oil, orange oil, sage oil, rosemary oil, cinnamon oil, pimento oil, cinnamon leaf oil, wintergreen oil, clove oil, eucalyptus oil and the like.

EXAMPLES

Following examples are illustrative but no way limits the scope of the invention Example-1

(Table-1) Dexibuprofen non-alcoholic transdeimal hydrogel prepared by using carbopol as gelling polymer:

| Sr. No | Ingredients | % by weight |
|---|---|---|
| 1. | Dexibuprofen | 10.00 |
| 2. | Carbopol 971P | 2.50 |
| 3. | Transcutol-P | 3.30 |
| 4. | Triethanolamine | 7.20 |
| 5. | Propylene glycol | 1.00 |
| 6. | Polyethylene glycol 400 | 1.00 |
| 7. | Menthol | 0.05 |
| 8. | Sodium metabisulphite | 0.20 |
| 9. | Sodium benzoate | 0.20 |
| 10. | Lavender oil | 0.05 |
| 11. | Purified water | q.s to make 100 |
| | Total | 100.00 |

Manufacturing procedure of example 1:
1. Disperse the Carbopol 971P in purified water under stirring for 15 minutes and allow it to soak overnight.

2. Dissolve sodium metabisulphite and sodium benzoate in purified water and then disperse dexibuprofen in it.

3. Dissolve menthol in triethanolamine.

4. Add step 3 to step 2 with constant stirring to get clear solution.

5. Mix propylene glycol and PEG 400, add this mixture to transcutol-P followed by lavender oil and mix well.

6. Add step 5 to step 4 and mix well.

7. Finally add step 6 to step 1 with constant stirring to obtain homogenous gel.

Example-2

(Table-2) Dexibuprofen non-alcoholic transdermal hydrogel prepared by using HPMC as gelling polymer:

| Sr. No | Ingredients | % by weight |
| --- | --- | --- |
| 1. | Dexibuprofen | 10.0 |
| 2. | HPMC K4M | 2.5 |
| 3. | HPMC E5 | 0.3 |
| 4. | Lutrol F68 | 5.0 |
| 5. | Transcutol-P | 3.3 |
| 6. | Propylene glycol | 1.0 |
| 7. | Polyethylene glycol 400 | 3.0 |
| 8. | Menthol | 0.1 |
| 9. | Sodium metabisulphite | 0.2 |
| 10. | Sodium benzoate | 0.2 |
| 11. | Triethanolamine | 7.2 |
| 12. | Simethicone | 0.00016 |
| 13. | Lavender oil | 0.1 |
| 14. | Purified water | q.s to make 100 |
| | Total | 100.0 |

Manufacturing procedure of example 2:

1. Disperse HPMC K4M, HPMC E5, Lutrol F68 in purified water under stirring for 15 minutes, and allow it to soak overnight.

2. Add simethicone to step 1 and mix well.

3. Dissolve sodium metabisulphite and sodium benzoate in water and then disperse dexibuprofen in it.

4. Dissolve menthol in triethanolamine.

5. Add step 4 to step 3 with constant stirring to get clear solution.

6. Mix propylene glycol, PEG 400 and add this mixture to transcutol-P followed by lavender oil and mixed well.

7. Add step 6 to step 5.

8. Add Step 7 to step 2 with constant stirring to obtain a homogenous gel.

Example-3

(Table-3) Dexibuprofen non-alcoholic transdermal hydrogel prepared by using carbopol as gelling polymer:

| Sr. No | Ingredients | % by weight |
| --- | --- | --- |
| 1. | Dexibuprofen | 5.00 |
| 2. | Carbopol 971P | 2.50 |
| 3. | Transcutol-P | 3.30 |
| 4. | Triethanolamine | 7.20 |
| 5. | Propylene glycol | 1.00 |
| 6. | Polyethylene glycol 400 | 1.00 |
| 7. | Menthol | 0.05 |
| 8. | Sodium metabisulphite | 0.20 |
| 9. | Sodium benzoate | 0.20 |
| 10. | Lavender oil | 0.05 |
| 11. | Purified water | q.s to make 100 |
| | Total | 100.00 |

Manufacturing procedure of example 3:

1. Disperse the Carbopol 971P in purified water under stirring for 15 minutes and allow it to soak overnight.

2. Dissolve sodium metabisulphite and sodium benzoate in purified water and then disperse dexibuprofen in it.

3. Dissolve menthol in triethanolamine.

4. Add step 3 to step 2 with constant stirring to get clear solution.

5. Mix propylene glycol and PEG 400, add this mixture to transcutol-P followed by lavender oil and mix well.

6. Add step 5 to step 4 and mix well.

7. Finally add step 6 to step 1 with constant stirring to obtain homogenous gel.

Example-4

(Table-4) Dexibuprofen non-alcoholic transdermal hydrogel prepared by using HPMC as gelling polymer:

| Sr. No | Ingredients | % by weight |
| --- | --- | --- |
| 1. | Dexibuprofen | 5.0 |
| 2. | HPMC K4M | 2.5 |
| 3. | HPMC E5 | 0.3 |
| 4. | Lutrol F68 | 5.0 |
| 5. | Transcutol-P | 3.3 |
| 6. | Propylene glycol | 1.0 |
| 7. | Polyethylene glycol 400 | 3.0 |
| 8. | Menthol | 0.1 |
| 9. | Sodium metabisulphite | 0.2 |
| 10. | Sodium benzoate | 0.2 |
| 11. | Triethanolamine | 7.2 |
| 12. | Simethicone | 0.00016 |
| 13. | Lavender oil | 0.1 |
| 14. | Purified water | q.s to make 100 |
| | Total | 100.0 |

Manufacturing Procedure of Example 4:

1. Disperse HPMC K4M, HPMC E5, Lutrol F68 in purified water under stirring for 15 minutes, and allow it to soak overnight.

2. Add simethicone to step 1 and mix well.

3. Dissolve sodium metabisulphite and sodium benzoate in water and then disperse dexibuprofen in it.

4. Dissolve menthol in triethanolamine.

5. Add step 4 to step 3 with constant stirring to get clear solution.

6. Mix propylene glycol, PEG 400 and add this mixture to transcutol-P followed by lavender oil and mixed well.

7. Add step 6 to step 5.

8. Add Step 7 to step 2 with constant stirring to obtain a homogenous gel.

The experimental trials showed that the pH modifying agent, antioxidant and water miscible solvent are essential excipients for obtaining stable non-alcoholic transdermal hydrogel of dexibuprofen. The hydrogels prepared according to example 1 and 3 using carbopol as gelling polymer produced opaque gel, whereas hydrogels prepared according to example 2 and 4 using HPMC as gelling polymer produced transparent gel. Further the hydrogels prepared according to example 1, 2, 3 and 4 were subjected for stability study at 40° C./75% RH for 3 months in laminated tubes and there was no significant change with respect to physical description, pH, assay value and related substances.

TABLE 5

Stability data of dexibuprofen non-alcoholic transdermal hydrogels prepared according to example 1, 2, 3, and 4 at 40° C./75% RH is as follows.

| Test | Example | Initial | 1$^{st}$ month | 2$^{nd}$ month | 3$^{rd}$ month |
|---|---|---|---|---|---|
| Description | 1 | Opaque homogenous gel | Opaque homogenous gel | Opaque homogenous gel | Opaque homogenous gel |
|  | 2 | Transparent homogenous gel | Transparent homogenous gel | Transparent homogenous gel | Transparent homogenous gel |
|  | 3 | Opaque homogenous gel | Opaque homogenous gel | Opaque homogenous gel | Opaque homogenous gel |
|  | 4 | Transparent homogenous gel | Transparent homogenous gel | Transparent homogenous gel | Transparent homogenous gel |
| Assay | 1 | 100.85 | 100.00 | 100.9 | 99.30 |
|  | 2 | 97.30 | 97.70 | 98.80 | 99.50 |
|  | 3 | 100.80 | 100.10 | 99.95 | 99.15 |
|  | 4 | 97.30 | 97.70 | 97.70 | 97.85 |
| pH | 1 | 5.82 | 5.92 | 5.81 | 5.87 |
|  | 2 | 5.90 | 5.95 | 5.97 | 6.00 |
|  | 3 | 5.82 | 5.98 | 5.96 | 6.00 |
|  | 4 | 5.90 | 5.95 | 6.06 | 6.10 |

We claim:

1. A transdermal hydrogel composition consisting essentially of, by weight % of the composition,
   1% to 15% dexibuprofen;
   0.5% to 30% of a combination of three gelling agents wherein the first gelling agent is selected from one of HPMC K4M and hydroxy ethyl cellulose, the second gelling agent is HPMC E5, and the third gelling agent is poloxamer 188;
   0.1% to 20% of a permeation enhancer consisting of diethylene glycol monoethyl ether;
   sodium hydroxide;
   0.05% to 5% of an antioxidant consisting of sodium metabisulfite;
   two water miscible solvents consisting of polyethylene glycol and propylene glycol;
   one or more preservative;
   one or more soothing agent; and
   water to total 100%.

2. The transdermal hydrogel composition according to claim 1, wherein the one or more preservative consists of sodium benzoate, and the one or more soothing agent consists of menthol.

3. The transdermal hydrogel composition according to claim 1, wherein the weight % of dexibuprofen is 10%.

4. The transdermal hydrogel composition according to claim 1, wherein the weight % of dexibuprofen is 5%.

* * * * *